(12) United States Patent
Werner et al.

(10) Patent No.: US 8,426,212 B2
(45) Date of Patent: Apr. 23, 2013

(54) METHOD AND SYSTEM FOR MONITORING FOR THE PRESENCE OF PHOSPHATE ESTERS IN JET FUEL

(75) Inventors: Gregory J. Werner, Puyallup, WA (US); Gary Robert Tamas, Kirkland, WA (US)

(73) Assignee: The Boeing Company, Chicago, IL (US)

( * ) Notice: Subject to any disclaimer, the term of this patent is extended or adjusted under 35 U.S.C. 154(b) by 105 days.

(21) Appl. No.: 12/899,526

(22) Filed: Oct. 6, 2010

(65) Prior Publication Data

US 2012/0085147 A1     Apr. 12, 2012

(51) Int. Cl.
*G01N 33/22* (2006.01)
(52) U.S. Cl.
USPC ........... 436/104; 436/127; 436/161; 436/173; 436/177; 436/178
(58) Field of Classification Search .................. 436/104, 436/127, 161, 173, 177, 178
See application file for complete search history.

(56) References Cited

U.S. PATENT DOCUMENTS 5,677,432 A * 10/1997 Jones et al. .................... 530/404

FOREIGN PATENT DOCUMENTS

SU          387275 A1     6/1973

OTHER PUBLICATIONS

Schenck et al. "Screening procedure for organochlorine and organophosphorus pesticide residues in milk using matrix solid phase dispersion (MSPD) extraction and gas chromatographic determination", Food Addit. Contam., 1995, 12(4):535-41 (Abstract).*

E. Spila et al., "Determination of Organophosphate Contaminants in Jet Fuel", Journal of Chromatography A, 1999, pp. 331-337, 847, Elsevier Science B.V.
D'Agostino et al., "Capillary column gas chromatographic-tandem mass spectrometric analysis of phosphate esters in the presence of interfering hydrocarbons", Journal of Chromatography A, 670 (1994) 127-134, Elsevier.
Habboush et al., "Extraction-gas chromatographic method for the determination of organophosphorus compounds as lubricating oil additives", Journal of Chromatography A, 696 (1995) 257-263, Elsevier.
Solbu et al., "Determination of airborne trialkyl and triaryl organophosphates originating from hydraulic fluids by gas chromatography-mass spectrometry Development of methodology for combined aerosol and vapor sampling", Journal of Chromatography A, 1161 (2007) 275-283, ScienceDirect, Elsevier.
Spila et al., "Determination of organophosphate contaminants in jet fuel", Journal of Chromatography A, 847 (1999) 331-337, Elsevier.
International Search Report and Written Opinion of the International Searching Authority for Counterpart PCT/US2011/049320, Mailed Dec. 5, 2011, 11 pages.

* cited by examiner

*Primary Examiner* — Jill Warden
*Assistant Examiner* — Monique Cole

(57) ABSTRACT

There is provided a method of monitoring for the presence of phosphate esters in jet fuel. The method comprises obtaining from a jet fuel source a jet fuel test sample suspected of containing phosphate esters. The method further comprises combining the jet fuel test sample with a polar solvent and a nonpolar solvent to form a mixture. The method further comprises agitating the mixture. The method further comprises extracting the polar solvent from the mixture. The method further comprises performing a combined gas chromatography and mass spectrometer analysis of the polar solvent to monitor for the presence of any phosphate esters and to obtain an actual concentration level of any phosphate esters. The method further comprises comparing the actual concentration level of any phosphate esters with a calibration standard concentration of phosphate esters in clean jet fuel.

9 Claims, 6 Drawing Sheets

| CALIBRATION STANDARD (BY WEIGHT) | MASS LD-4 (gm) | MASS JET FUEL (gm) | * ACTUAL CONCENTRATION (ppm WEIGHT) |
|---|---|---|---|
| 500 ppm STOCK SOLUTION | 0.020 | 40.0 | 500 |

| CALIBRATION STANDARD (BY WEIGHT) | MASS STOCK SOLUTION (gm) | MASS JET FUEL (gm) | * ACTUAL CONCENTRATION (ppm WEIGHT) |
|---|---|---|---|
| 0 | 0 | 50 | 0 |
| 0.50 | 0.05 | 49.95 | 0.5 |
| 1.0 | 0.10 | 49.9 | 1.0 |
| 2.5 | 0.25 | 49.75 | 2.5 |
| 5.0 | 0.50 | 49.5 | 5.0 |

* EXACT CONCENTRATION VALUES WILL BE MADE AFTER WEIGHING

FIG. 5

METHOD AND SYSTEM FOR MONITORING FOR THE PRESENCE OF PHOSPHATE ESTERS IN JET FUEL

CROSS-REFERENCE TO RELATED APPLICATIONS (Not Applicable)

STATEMENT RE: FEDERALLY SPONSORED RESEARCH/DEVELOPMENT (Not Applicable)

FIELD

The disclosure relates generally to methods and systems for monitoring for the presence of chemical compounds in fuel, and more particularly, to methods and systems for monitoring for the presence of organophosphorus compounds in jet fuel.

BACKGROUND

Aircraft jet engines may be manufactured using cobalt containing metals and alloy materials. Such metals and alloy materials allow the aircraft jet engines to operate more efficiently by withstanding high temperatures and resisting oxidation and corrosion. However, such cobalt containing metals can be susceptible to corrosion when they react with organophosphorus compounds such as phosphate esters.

In known aviation hydraulic fluids used in the hydraulic systems of aircraft, phosphate esters are the most commonly used base stocks of which tributyl phosphate, isopropylated triphenyl phosphates, n-butyl diphenyl phosphate, and di-n-butyl phenyl phosphate are widely used components. Phosphate esters are typically used due to their fire resistance properties. For example, a known fire resistant aviation hydraulic fluid is SKYDROL, manufactured by Solutia Inc. of St. Louis Mo. (SKYDROL is a registered trademark of Solutia Inc. of St. Louis, Mo.) However, phosphate esters in such aviation hydraulic fluids are polar and tend to absorb atmospheric moisture readily and build up high concentrations of water, for example, 0.3% to 1% water, or more. This can result in the formation of alcohols and acids which can adversely affect the force transmission properties of the hydraulic fluid or induce corrosion.

Such organophosphate-based aviation hydraulic fluids may be used in pumps in jet fuel tanks on a jet aircraft having jet engines manufactured using cobalt containing metals. Due to complete immersion of the pumps in the jet fuel tanks, jet fuel contamination by phosphate esters from organophosphate-based aviation hydraulic fluids can occur and subsequent corrosion of the jet engine can result. In order to prevent contamination of the jet fuel and protect the integrity of the jet engine, the jet fuel should be periodically checked to monitor for the presence of any phosphate esters from organophosphate-based aviation hydraulic fluid. While jet engines not manufactured using cobalt containing metals typically require a concentration level of less than one thousand (1000) parts per million (ppm) of such phosphate esters from organophosphate-based aviation hydraulic fluid in the jet fuel tested, jet engines manufactured using cobalt containing metals require a concentration level of less than one (1) ppm of such phosphate esters from organophosphate-based aviation hydraulic fluid in the jet fuel tested.

Techniques are known for testing jet fuel for detection of organophosphorus compounds, such as phosphate esters from organophosphate-based aviation hydraulic fluid. Such known techniques include inductively coupled plasma spectroscopy and known gas chromatography/mass spectrometry methodologies. However, such known techniques are capable of detecting organophosphorus compounds, such as phosphate esters from organophosphate-based aviation hydraulic fluid in jet fuel, at a concentration level of, at best, ten (10) ppm. Such concentration level is not sufficient for the detection requirement of less than one (1) ppm for jet engines manufactured using cobalt containing metals.

Accordingly, there is a need in the art for a method and system for detecting the required small concentration level of organophosphorus compounds, such as phosphate esters in jet fuel, that provides advantages over known methods and systems.

SUMMARY

This need for a method and system for detecting the required small concentration level of organophosphorus compounds, such as phosphate esters in jet fuel, is satisfied. As discussed in the below detailed description, embodiments of the method and system may provide significant advantages over existing methods and systems.

In an embodiment of the disclosure, there is provided a method of monitoring for the presence of phosphate esters in jet fuel. The method comprises obtaining from a jet fuel source a jet fuel test sample. The method further comprises combining the jet fuel test sample with a polar solvent and a nonpolar solvent to form a mixture. The method further comprises agitating the mixture. The method further comprises extracting the polar solvent from the mixture. The method further comprises performing a combined gas chromatography and mass spectrometer analysis of the polar solvent to monitor for the presence of any phosphate esters and to obtain an actual concentration level of any phosphate esters. The method further comprises comparing the actual concentration level of any phosphate esters with a calibration standard concentration of phosphate esters in clean jet fuel.

In another embodiment of the disclosure, there is provided an in-line system for monitoring for the presence of phosphate esters in jet fuel on an aircraft. The system comprises a preloaded sample vessel containing a polar solvent and a nonpolar solvent. The system further comprises a jet fuel test sample. The system further comprises a transfer element for transferring the jet fuel test sample to the preloaded sample vessel. The system further comprises an agitating device for mixing the jet fuel test sample with the polar solvent and the nonpolar solvent in the preloaded sample vessel in order to form a mixture. The system further comprises a separating device for separating the polar solvent from the mixture. The system further comprises a portable combined gas chromatography and mass spectrometer apparatus coupled to the separating device. The combined gas chromatography and mass spectrometer apparatus has a receiving element for receiving the polar solvent from the separating device so that the combined gas chromatography and mass spectrometer apparatus can analyze the polar solvent to monitor for the presence of any phosphate esters and to obtain an actual concentration level of any phosphate esters. The system further comprises a calibration concentration standard of phosphate esters in clean jet fuel for comparing to the actual concentration level of any phosphate esters.

In another embodiment of the disclosure, there is provided a portable field kit for monitoring for the presence of phosphate esters in jet fuel in a ground-based airport fuel supply system. The field kit comprises a preloaded sample vessel containing a polar solvent and a nonpolar solvent. The field kit further comprises a jet fuel test sample. The field kit further comprises a transfer element for transferring the jet fuel test sample to the preloaded sample vessel. The field kit further comprises an agitating device for mixing the jet fuel test sample with the polar solvent and the nonpolar solvent in the preloaded sample vessel in order to form a mixture. The field kit further comprises a separating device for separating the polar solvent from the mixture. The field kit further comprises a portable combined gas chromatography and mass spectrometer apparatus coupled to the separating device. The combined gas chromatography and mass spectrometer apparatus has a receiving element for receiving the polar solvent from the separating device so that the combined gas chromatography and mass spectrometer apparatus can analyze the polar solvent to monitor for the presence of any phosphate esters and to obtain an actual concentration level of any phosphate esters. The field kit further comprises a calibration concentration standard of phosphate esters in clean jet fuel for comparing to the actual concentration level of any phosphate esters.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein:

FIG. 5 is an illustration of a table showing the results of the calibration standards and samples prepared in a laboratory preparation and analysis procedure; and, FIG. 6 is a flow diagram illustrating an exemplary method of the disclosure of monitoring for the presence of phosphate esters in jet fuel.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art.

Figure 1:
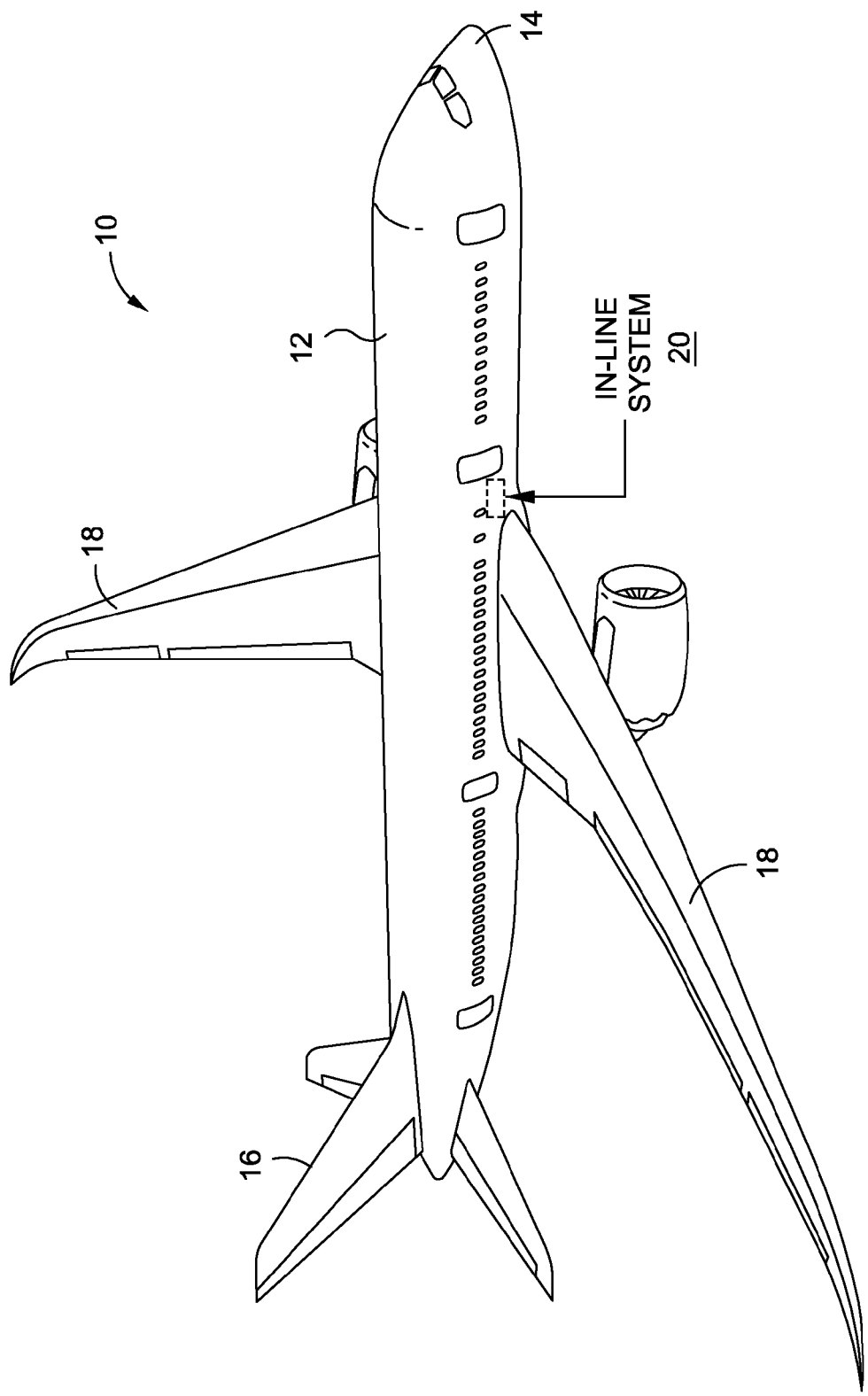
FIG. 1 is an illustration of a perspective view of an aircraft having an exemplary embodiment of an in-line system of the disclosure for monitoring for the presence of phosphate esters in jet fuel.

Now referring to the Figures, FIG. 1 is an illustration of a perspective view of an aircraft 10 having a fuselage 12, a nose portion 14, a tail portion 16, and wings 18. The aircraft 10 is shown with an exemplary embodiment of an in-line system 20 for monitoring for the presence of phosphate esters in jet fuel, discussed in detail below.

Figure 6:
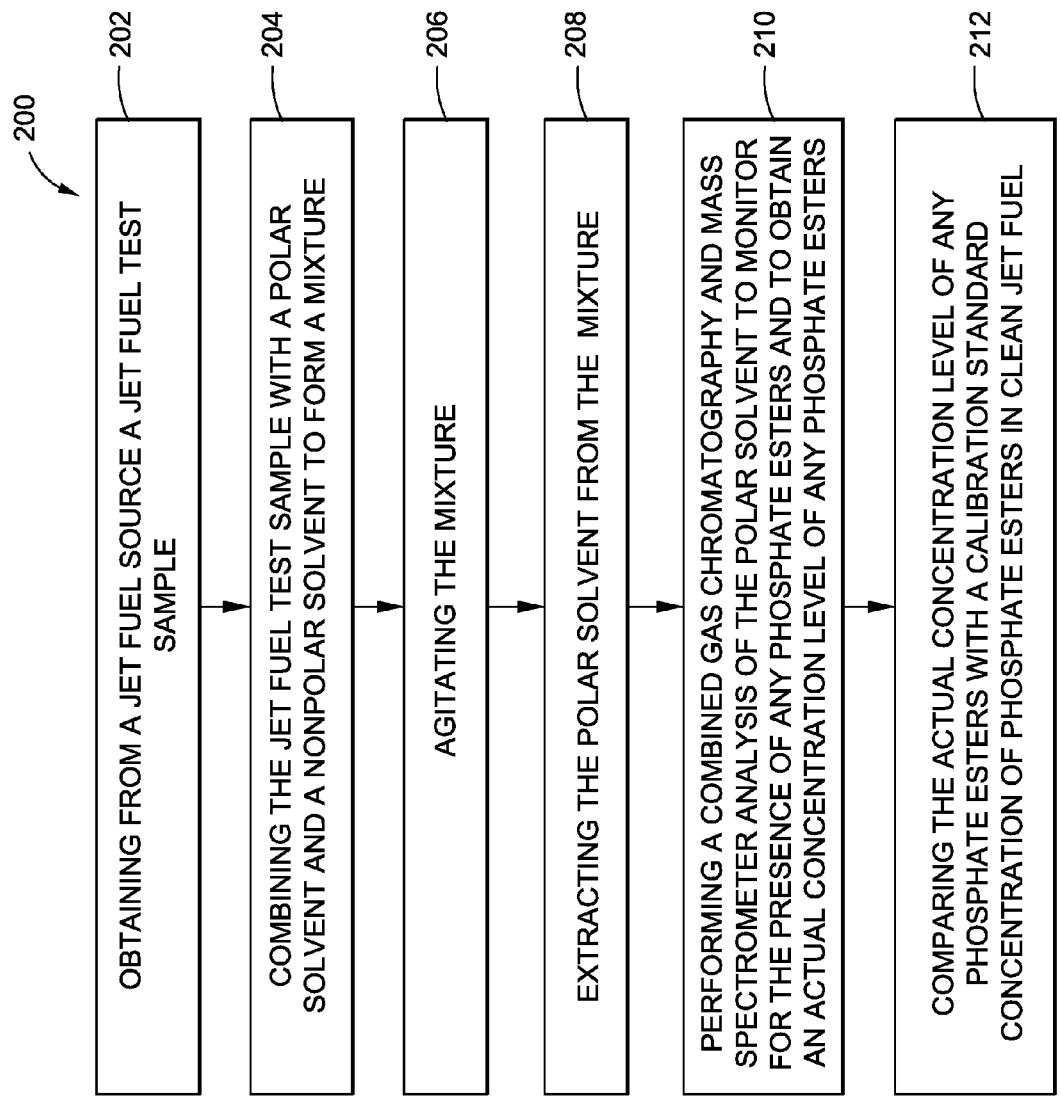

In one embodiment of the disclosure, there is provided a quantitative analytical method 200 of monitoring for the presence of phosphate esters in jet fuel. FIG. 6 is a flow diagram illustrating the exemplary method 200 of the disclosure. The method 200 comprises step 202 of obtaining from a jet fuel source 38 (see FIG. 2) or 86 (see FIG. 4) a jet fuel test sample 42 (see FIGS. 2, 4). The jet fuel sample 42 may be suspected of containing phosphate esters 40 (see FIGS. 2, 4). The method 200 further comprises step 204 of combining the jet fuel test sample 42 with a polar solvent 24 (see FIGS. 2, 4) and a nonpolar solvent 26 (see FIGS. 2, 4) to form a mixture 52 (see FIGS. 2, 4). The jet fuel test sample 42 may be transferred via a transfer element 44 to a preloaded sample vessel 22 containing the polar solvent 24 and the nonpolar solvent 26. Preferably, the transfer element 44 comprises a fuel line, a fuel pipe, or another suitable transfer element for transferring and transporting the jet fuel test sample 42. Do not specify polar index ranges. The polar solvent 24 preferably comprises acetonitrile (ACN) 30 or another suitable polar solvent. The polarity index of ACN is 5.8. For purposes of this application, "polarity index" is defined as a relative measure of the degree of interaction of a solvent with various polar test solutes. The nonpolar solvent 26 preferably comprises petroleum ether (PET) 28 or another suitable nonpolar solvent. The polarity index of PET is 0.1.

The method 200 further comprises step 206 of agitating the mixture 52. Preferably, the agitating step 206 is performed with an agitating device 48 comprising an automated vortex mixer 50 coupled to a mixing station 46. However, the agitating device 48 may also comprise a shaker table or another suitable agitating or mixing device. Alternatively, the agitating step 206 may be performed by manually shaking or agitating the mixture 52 in the preloaded sample vessel 22. Preferably, the jet fuel test sample 42 is mixed with the acetonitrile (ACN) 30 and the petroleum ether (PET) in a range of from about one (1) minute to about twelve (12) minutes, and more preferably, for about ten (10) minutes. The method 200 further comprises step 208 of extracting a portion 60 (see FIGS. 2, 4) of the polar solvent 24 from the mixture 52. The extracting step 208 is performed with a separating device 54 that is used to separate or extract a portion 60 of the polar solvent 24 from the mixture 52. Preferably, the separating device 54 comprises an extraction element 56, such as a robotic autosampler needle, a rotatable syringe, or another suitable extraction element for extracting the portion 60 or aliquot of the polar solvent 24, such as the acetonitrile (ACN) 30, from the preloaded sample vessel 22 with the mixture 52 and the acetonitrile (ACN) 30. Preferably, the extraction element 56 is housed within an injector element 58, such as a tubing or container portion, for holding the portion 60 of the polar solvent 24, such as the acetonitrile (ACN) 30, once it is extracted by the extraction element 56. The separating device 54 is further used to inject the extracted or separated portion 60 of the polar solvent 24 into a receiving element 66 of a combined gas chromatography and mass spectrometer apparatus 70.

The method 200 further comprises step 210 of performing a combined gas chromatography and mass spectrometer analysis of the portion 60 of the polar solvent 24 to monitor for the presence of any phosphate esters 40 and to obtain an actual concentration level 82 (see FIGS. 2, 4) of any phosphate esters 40. The combined gas chromatography and mass spectrometer analysis is performed with the combined gas chromatography and mass spectrometer apparatus 70 which is preferably coupled to the mixing station 46 and the separating device 54. The combined gas chromatography and mass spectrometer analysis is preferably performed in an amount of time in a range of from about 5 minutes to about 10 minutes. Preferably, the step 210 of performing the combined gas chromatography and mass spectrometer analysis is performed with the combined gas chromatography and mass spectrometer apparatus 70, and preferably, the combined gas chromatography and mass spectrometer apparatus 70 is portable. The combined gas chromatography and mass spectrometer apparatus 70 in portable form may have a weight in the range of from about thirty (30) pounds to about fifty (50) pounds, and more preferably about thirty-five (35) pounds.

The combined gas chromatography and mass spectrometer apparatus 70 comprises the receiving element 66 for receiving the extracted or separated portion 60 of the polar solvent 24 from the separating device 54. Preferably, the receiving element 66 comprises an injection port 68. The combined gas chromatography and mass spectrometer apparatus 70 further comprises a separation element 76 coupled to the receiving element 66 via inlet 72. The separation element 76 preferably comprises a capillary or open tubular column such as a wall-coated open tubular or support-coated open tubular column, or another suitable separation element. The capillary column preferably comprises a wall-coated open tubular column having an internal diameter of about 0.18 mm (millimeters) to about 0.25 mm. The capillary column is preferably coated with a material comprising fused silica or another suitable material. The capillary column is preferably coiled and about twenty (20) meters in length.

The combined gas chromatography and mass spectrometer apparatus 70 further comprises a mass spectrometer 78 coupled to the separation element 76 via connector element 77. The mass spectrometer 78 combines a high sensitivity with being able to determine the molecular composition of the portion 60 of the polar solvent 24. The combined gas chromatography and mass spectrometer apparatus 70 further comprises a gas chromatography portion 74. Preferably, the gas chromatography portion 74 comprises an oven that can be heated to a temperature of from about 130 degrees C. to about 250 degrees C. during the analysis and depending on the material being heated. The combined gas chromatography and mass spectrometer apparatus 70 analyzes the portion 60 of the polar solvent 24 to monitor for the presence of any phosphate esters 40 and to obtain an actual concentration level 82 of any phosphate esters 40 present in the jet fuel test sample 42. The combined gas chromatography and mass spectrometer apparatus 70 is preferably controlled by a controller 80 (see FIGS. 2, 4). The controller 80 preferably comprises a computer or another suitable controller device.

Figure 2:
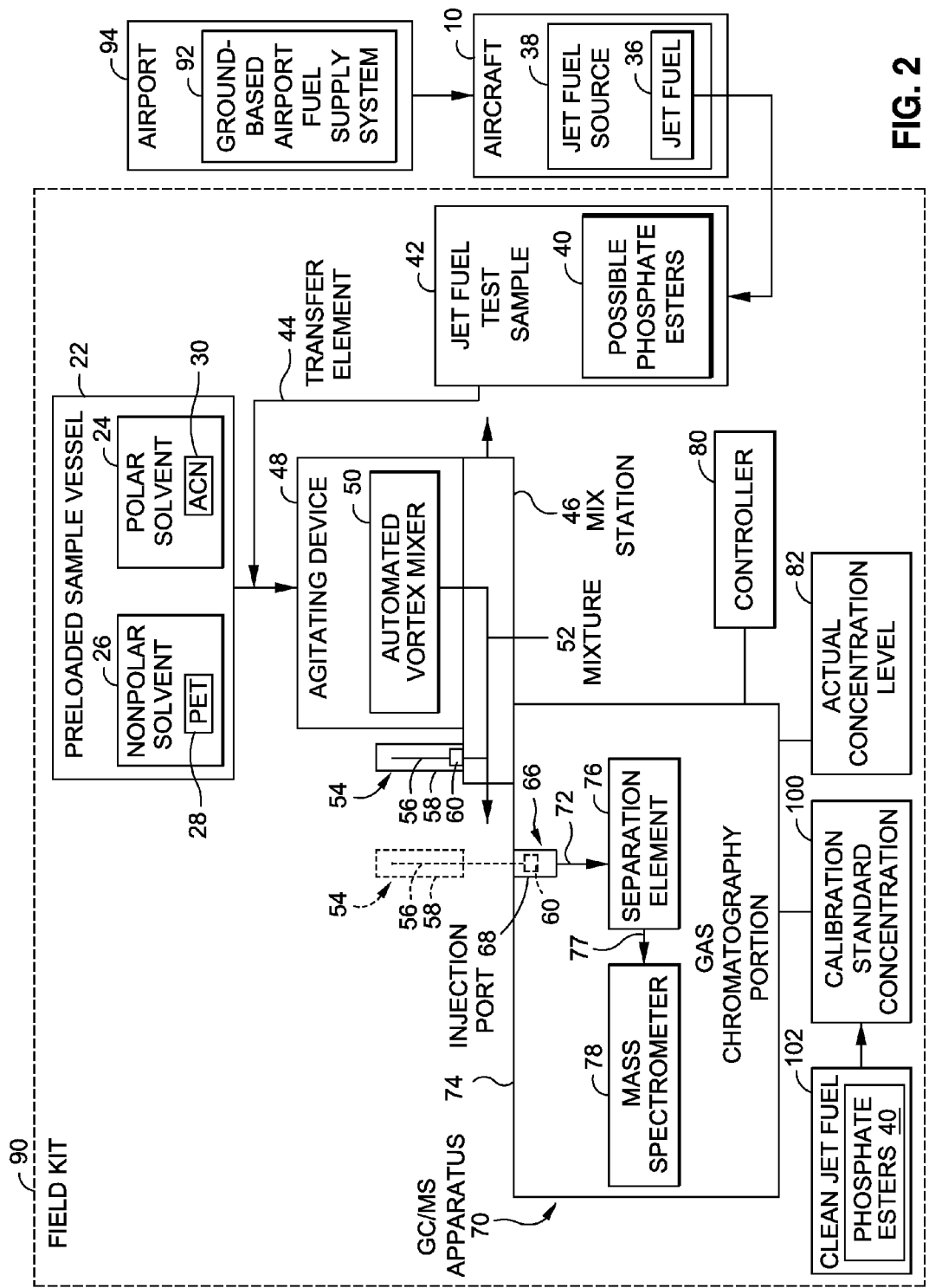
FIG. 2 is an illustration of a schematic diagram of an embodiment of a field kit of the disclosure for monitoring for the presence of phosphate esters in jet fuel.

The method 200 further comprises step 212 of comparing the actual concentration level 82 of any phosphate esters 40 present in the ACN portion 60 of the polar solvent with a calibration standard concentration 100 of phosphate esters 40 in clean jet fuel 102 (see FIG. 2). The method 200 monitors for the presence of phosphate esters 40 in jet fuel at a concentration level of less than one (1) part per million (ppm). The total amount of time to perform the entire method 200 may comprise an amount of time in a range of from about twenty (20) minutes to about thirty (30) minutes.

The portion 60 of the polar acetonitrile (ACN) 30 is analyzed with the combined gas chromatography and mass spectrometer apparatus 70 to find one or more organophosphorus compounds, preferably phosphate esters, and more preferably, SKYDROL, and most preferably, SKYDROL LD-4 Type IV, Class 1, fire resistant aviation hydraulic fluid from Solutia Inc. of St. Louis, Mo. (SKYDROL is a registered trademark of Solutia Inc. of St. Louis, Mo.) SKYDROL LD-4 is a low density fluid with an average concentration of 58.2% by weight of tributyl phosphate, 20-30% by weight dibutyl phenyl phosphate, 5-10% by weight butyl diphenyl phosphate, less than 10% by weight 2-ethylhexyl 7-oxabicyclo [4.1.0]heptane-3-carboxylate, and 1-5% by weight 2,6-di-tert-butyl-p-cresol. SKYDROL LD-4 has a specific gravity of 1.004-1.014 at 25 degrees Celsius, a viscosity of 10.8-11.6 cSt (CentiStokes) at 38 degrees Celsius, a flash point of 160 degrees Celsius, and an autoignition temperature of 398 degrees Celsius.

The gas chromatography portion 74 is preferably used to separate the compound of interest, in this case, the phosphate ester. The separation is preferably performed with the separation element 76, in the form of a capillary column, so that the compound of interest can be separated and then detected with the mass spectrometer 78. The mass spectrometer 78 works by atomizing and ionizing the compound of interest received from the separation element 76 into its constituent elements or molecular fragments of the parent molecule using a high-energy source, such as a high-energy electron beam (not shown). The mass spectrometer 78 acts as a detector and measures the mass spectrum of signal strength data as a function of mass-to-charge ratio. In a mass spectrum, the signal strength data may be in the form of peaks of a chromatogram of signal intensity as a function of mass-to-charge ratio. The intensity of the peak is generally associated with the apex of the peak. Generally, the mass-to-charge ratio relates to the molecular weight of the compound of interest. The components of the compound of interest may be ionized by various methods such as impacting them with an electron beam or another suitable method which results in the formation of charged particles (ions). The positive ions are then accelerated by an electric field. A mass-to-charge ratio (m/z) of the particles based on the details of motion of the ions as they transit through electromagnetic fields is computed, and detection of the ions which were sorted according to mass-to-charge ratio is obtained.

In another embodiment of the disclosure, as shown in FIG. 2, there is provided a portable field kit 90 for monitoring for the presence of phosphate esters 40 in jet fuel in a ground-based airport fuel supply system 92 at an airport 94. FIG. 2 is an illustration of a schematic diagram of an embodiment of the field kit system 90 of the disclosure. The method 200 may be performed with the field kit 90 to monitor for the presence of phosphate esters in jet fuel in the ground-based airport fuel supply system 92 at the airport 94 (see FIG. 2). With the field kit 90, the jet fuel test sample 42 is preferably obtained from an aircraft 10 that is being supplied with jet fuel from the ground-based airport fuel supply system 92. Alternatively, the jet fuel test sample 42 may be obtained directly from the ground-based airport fuel supply system 92 that supplies the jet fuel to the aircraft 10.

As shown in FIG. 2, the field kit 90 comprises a preloaded sample vessel 22 containing a polar solvent 24 and a nonpolar solvent 26. Preferably, the polar solvent 24 is acetonitrile (ACN) 30 or another suitable polar solvent. Preferably, the nonpolar solvent 26 is petroleum ether (PET) 28 or another suitable nonpolar solvent. The field kit 90 further comprises a jet fuel test sample 42. The jet fuel test sample 42 may be suspected of containing possible phosphate esters 40. Preferably, the jet fuel test sample 42 is obtained from jet fuel 36 from a jet fuel source 38. Preferably, the jet fuel source 38 is obtained from an aircraft 10 that is being supplied with jet fuel from a ground-based airport fuel supply system 92 at an airport 94.

The field kit 90 further comprises a transfer element 44 for transferring the jet fuel test sample 42 to the preloaded sample vessel 22. Preferably, the transfer element 44 comprises a fuel line, a fuel pipe, or another suitable transfer element for transferring and transporting the jet fuel test sample 42 from the jet fuel source 38 to the preloaded sample vessel 22. The field kit 90 further comprises an agitating device 48 for mixing the jet fuel test sample 42 with the polar solvent 24 and the nonpolar solvent 26 in the preloaded sample vessel 22 in order to form a mixture 52. Preferably, the agitating device 48 comprises an automated vortex mixer 50 coupled to a mixing station 46. However, the agitating device 48 may also comprise a shaker table or another suitable agitating or mixing device. Alternatively, the mixture 52 in the preloaded sample vessel 22 may be manually shaken or agitated. The field kit 90 further comprises a separating device 54 for separating or extracting a portion 60 of the polar solvent 24 from the mixture 52. Preferably, the separating device 54 comprises an extraction element 56, such as a robotic autosampler needle, a rotatable syringe, or another suitable extraction element for extracting the portion 60 or aliquot of the polar solvent 24, such as the acetonitrile (ACN) 30, from the preloaded sample vessel 22 with the mixture 52 and the acetonitrile (ACN) 30. Preferably, the extraction element 56 is housed within an injector element 58, such as a tubing or container portion, for holding the portion 60 of the acetonitrile (ACN) 30 once it is extracted by the extraction element 56. The separating device 54 is further used to inject the extracted or separated portion 60 of the polar solvent 24 into a receiving element 66 of the combined gas chromatography and mass spectrometer apparatus 70.

The field kit 90 further comprises the combined gas chromatography and mass spectrometer apparatus 70 preferably coupled to the mixing station 46 and the separating device 54. Preferably, the combined gas chromatography and mass spectrometer apparatus 70 is portable. The combined gas chromatography and mass spectrometer apparatus 70 in portable form may have a weight in the range of from about thirty (30) pounds to about fifty (50) pounds, and more preferably about thirty-five (35) pounds. The combined gas chromatography and mass spectrometer apparatus 70 comprises a receiving element 66 for receiving the portion 60 of the polar solvent 24 from the mixture 52. Preferably, the receiving element 66 comprises an injection port 68. The combined gas chromatography and mass spectrometer apparatus 70 further comprises a separation element 76 coupled to the receiving element 66 via inlet 72. The separation element 76 preferably comprises a capillary or open tubular column such as a wall-coated open tubular or support-coated open tubular column, or another suitable separation element. The capillary column preferably comprises a wall-coated open tubular column having an internal diameter of about 0.18 mm (millimeters) to about 0.25 mm. The capillary column is preferably coated with a material comprising fused silica or another suitable material. The capillary column is preferably coiled and about twenty (20) meters in length.

The combined gas chromatography and mass spectrometer apparatus 70 further comprises a mass spectrometer 78 coupled to the separation element 76 via connector element 77. The mass spectrometer 78 combines a high sensitivity with being able to determine the molecular composition of the portion 60 of the polar solvent 24. The combined gas chromatography and mass spectrometer apparatus 70 further comprises a gas chromatography portion 74. Preferably, the gas chromatography portion 74 comprises an oven that can be heated to a temperature of from about 130 degrees C. to about 250 degrees C. depending on the material being heated. The combined gas chromatography and mass spectrometer apparatus 70 analyzes the portion 60 of the polar solvent 24 to monitor for the presence of any phosphate esters 40 and to obtain an actual concentration level 82 of any phosphate esters 40 present in the jet fuel test sample 42. The field kit 90 further comprises a calibration concentration standard 100 of phosphate esters 40 in clean jet fuel 102 for comparing to the actual concentration level 82 of any phosphate esters present in the jet fuel test sample 42. The field kit 90 further comprises a controller 80 for controlling the combined gas chromatography and mass spectrometer apparatus 70. The controller 80 preferably comprises a computer or another suitable controller device. The field kit 90 is preferably used to monitor for the presence of phosphate esters in jet fuel at a concentration level of less than one (1) part per million (ppm).

Figure 3:
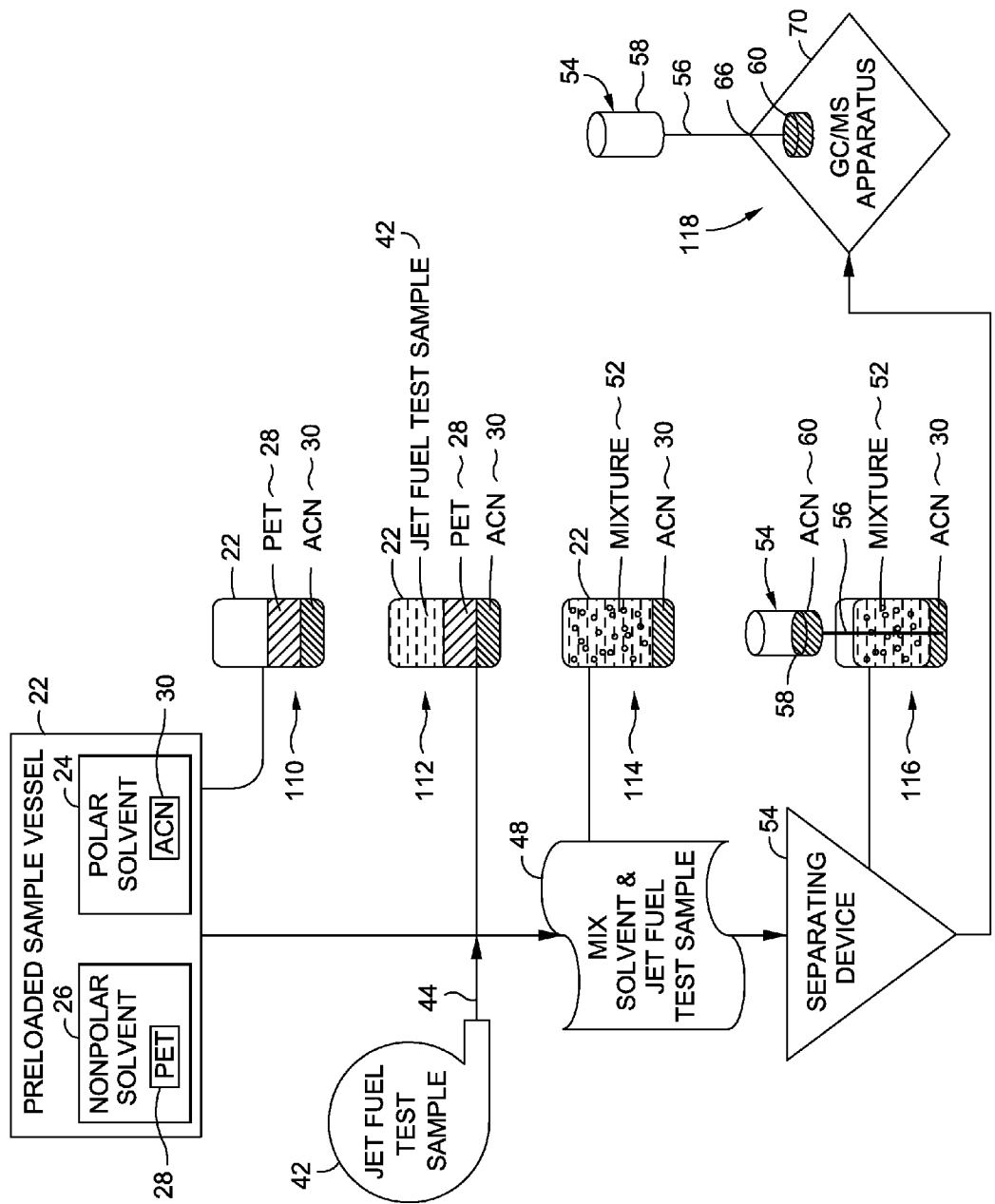
FIG. 3 is an illustration of a schematic flow diagram illustrating various stages of an exemplary mixture used in one or more embodiments of the systems and methods of the disclosure.

FIG. 3 is an illustration of a schematic flow diagram illustrating various stages of an exemplary mixture used in one or more embodiments of the systems and methods of the disclosure. FIG. 3 shows the preloaded sample vessel 22 containing the polar solvent 24, preferably acetonitrile (ACN) 30, and containing the nonpolar solvent 26, preferably petroleum ether (PET) 28. As shown in FIG. 3, the preloaded sample vessel 22 in stage 110 shows the acetonitrile (ACN) 30 in a layer at the bottom of the vessel 22 and the petroleum ether (PET) 28 in a separate layer on top of the acetonitrile (ACN) 30 layer. The jet fuel test sample 42 is then transferred or added via the transfer element 42 into the preloaded sample vessel 22 with the acetonitrile (ACN) 30 and petroleum ether (PET) 28. As shown in FIG. 3, the preloaded sample vessel in stage 112 shows the acetonitrile (ACN) 30 in a layer at the bottom of the vessel 22, the petroleum ether (PET) 28 in a separate layer on top of the acetonitrile (ACN) 30 layer, and the jet fuel test sample 42 in a separate layer on top of the petroleum ether (PET) 28 layer. The preloaded sample vessel 22 is then mixed with an agitating device 48, preferably in the form of an automated vortex mixer 50 (see FIG. 2), for a predetermined amount of time to form a mixture 52. Preferably, the jet fuel test sample 42 is mixed with the acetonitrile (ACN) 30 and the petroleum ether (PET) in a range of from about one (1) minute to about twelve (12) minutes, and more preferably, for about ten (10) minutes. As shown in FIG. 3, the preloaded sample vessel 22 in stage 114 shows the acetonitrile (ACN) 30 in a layer at the bottom of the vessel 22 and the mixture 52 of the jet fuel test sample 42 and the petroleum ether (PET) 28 in a separate layer on top of the acetonitrile (ACN) 30 layer. The mixture 52 may contain a residual amount of ACN. After the mixture 42 is formed, the separating device 54 is used to extract a portion 60 of the acetonitrile (ACN) 30 from the preloaded sample vessel 22 with the mixture 52 and the acetonitrile (ACN) 30. Preferably, the separating device 54 comprises the extraction element 56, such as a robotic autosampler needle or rotatable syringe, for extracting the portion 60 or aliquot of the acetonitrile (ACN) 30 from the preloaded sample vessel 22 with the mixture 52 and the acetonitrile (ACN) 30. Preferably, the extraction element 56 is housed within an injector element 58, such as a tubing or container portion, for holding the portion 60 of the acetonitrile (ACN) 30 once it is extracted by the extraction element 56. As shown in FIG. 3, the preloaded sample vessel 22 in stage 116 shows the extraction element 56 of the separating device 54 extracting the portion 60 of the acetonitrile (ACN) 30 in the layer at the bottom of the vessel 22 from the preloaded sample vessel 22 containing the mixture 52 and the acetonitrile (ACN) 30 layer. The extraction element 56 extracts the portion 60 of the acetonitrile (ACN) 30 and draws it into the injector element 58. As shown in FIG. 3, stage 118 shows the injector element 58 and extraction element 56 of the separating device 54 injecting the portion 60 of the acetonitrile (ACN) 30 into the receiving element 66, preferably in the form of injection port 68 (see FIG. 2), of the combined gas chromatography and mass spectrometer apparatus 70 for analysis. The sample analysis with the combined gas chromatography and mass spectrometer apparatus 70 may be completed in less than ten (10) minutes and preferably, may be completed in less than five (5) minutes.

Figure 4:
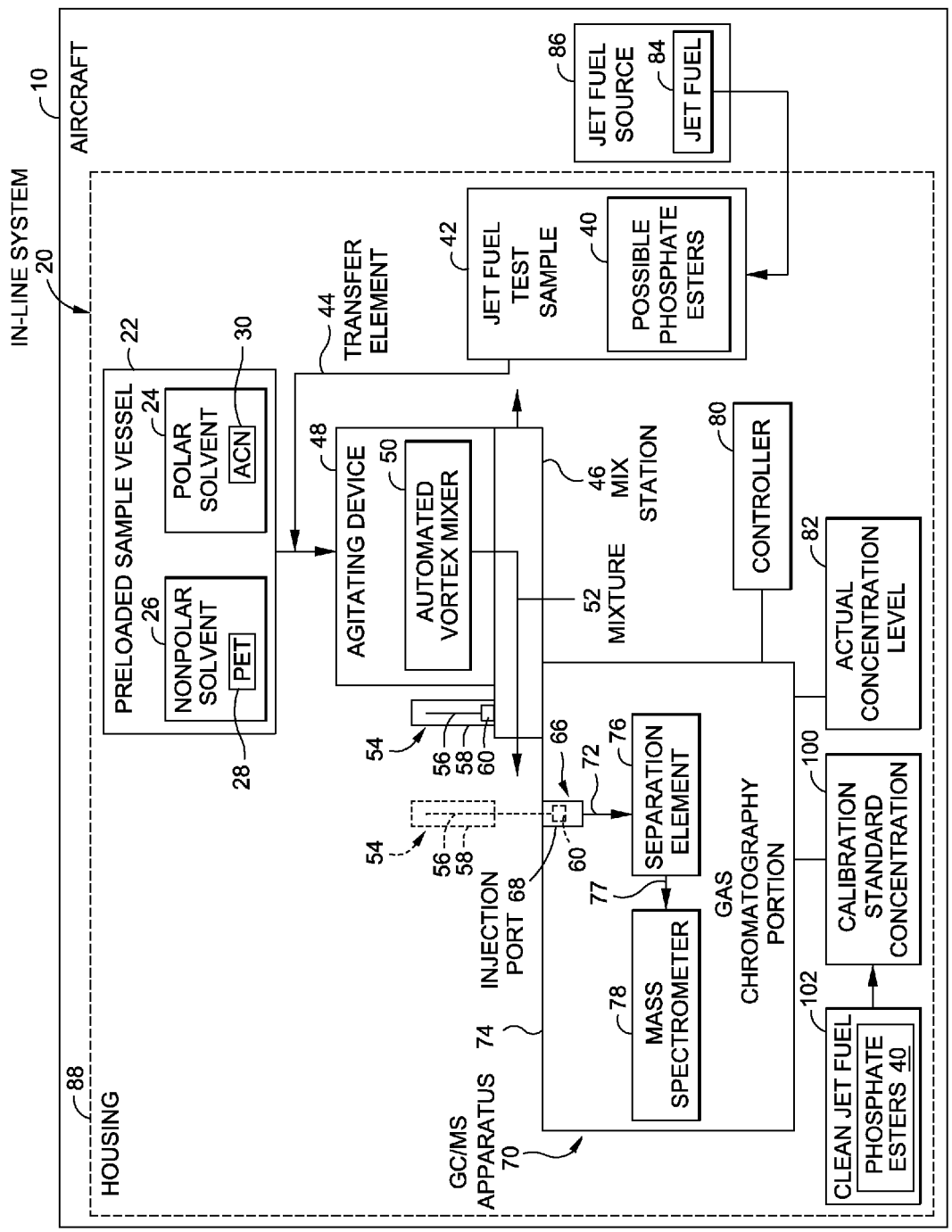
FIG. 4 is an illustration of a schematic diagram of an embodiment of an in-line system of the disclosure for monitoring for the presence of phosphate esters in jet fuel.

In another embodiment of the disclosure, as shown in FIG. 4, there is provided an in-line system 20 for monitoring for the presence of phosphate esters 40 in jet fuel on an aircraft 10. FIG. 4 is an illustration of a schematic diagram of an embodiment of the in-line system 20 of the disclosure. The method 200 may be performed with the in-line system 20 on the aircraft 10 (see FIGS. 1, 4). With the in-line system 20, the jet fuel test sample 42 is obtained from the aircraft 10 (see FIG. 1) in real time while the aircraft 10 is in flight. The in-line system 20 may comprise a housing 88 to house the components of the in-line system 20. The in-line system 20 further comprises a preloaded sample vessel 22 preferably containing a polar solvent 24 and a nonpolar solvent 26. Preferably, the polar solvent 24 is acetonitrile (ACN) 30 or another suitable polar solvent. Preferably, the nonpolar solvent 26 is petroleum ether (PET) 28 or another suitable nonpolar solvent. The in-line system 20 further comprises the jet fuel test sample 42. The jet fuel test sample 42 may be suspected of containing possible phosphate esters 40. Preferably, the jet fuel test sample 42 is obtained from jet fuel 84 from a jet fuel source 86. Preferably, the jet fuel source 86 is obtained from the aircraft 10 (see FIG. 1) in real time while the aircraft 10 is in flight.

The in-line system 20 further comprises a transfer element 44 for transferring the jet fuel test sample 42 to the preloaded sample vessel 22. Preferably, the transfer element 44 comprises a fuel line, a fuel pipe, or another suitable transfer element for transferring and transporting the jet fuel test sample 42 from the jet fuel source 86 to the preloaded sample vessel 22. The in-line system 20 further comprises an agitating device 48 for mixing the jet fuel test sample 42 with the polar solvent 24 and the nonpolar solvent 26 in the preloaded sample vessel 22 in order to form a mixture 52. Preferably, the agitating device 48 comprises an automated vortex mixer 50 coupled to a mixing station 46. However, the agitating device 48 may also comprise a shaker table or another suitable agitating or mixing device. Alternatively, the mixture 52 in the preloaded sample vessel 22 may be manually shaken or agitated.

The in-line system 20 further comprises a separating device 54 for separating or extracting a portion 60 of the polar solvent 24 from the mixture 52. Preferably, the separating device 54 comprises an extraction element 56, such as a robotic autosampler needle, a rotatable syringe, or another suitable extraction element for extracting the portion 60 or aliquot of the polar solvent 24, such as the acetonitrile (ACN) 30, from the preloaded sample vessel 22 with the mixture 52 and the acetonitrile (ACN) 30. Preferably, the extraction element 56 is housed within an injector element 58, such as a tubing or container portion, for holding the portion 60 of the acetonitrile (ACN) 30 once it is extracted by the extraction element 56. The separating device 54 is further used to inject the extracted or separated portion 60 of the polar solvent 24 into a receiving element 66 of a gas chromatography and mass spectrometer apparatus 70.

The in-line system 20 further comprises the combined gas chromatography and mass spectrometer apparatus 70 preferably coupled to the mixing station 46 and the separating device 54. Preferably, the combined gas chromatography and mass spectrometer apparatus 70 is portable. The combined gas chromatography and mass spectrometer apparatus 70 in portable form may have a weight in the range of from about thirty (30) pounds to about fifty (50) pounds, and more preferably about thirty-five (35) pounds. The combined gas chromatography and mass spectrometer apparatus 70 comprises a receiving element 66 for receiving the portion 60 of the polar solvent 24 from the mixture 52. Preferably, the receiving element 66 comprises an injection port 68. The combined gas chromatography and mass spectrometer apparatus 70 further comprises a separation element 76 coupled directly to the receiving element 66 via inlet 72. The separation element 76 preferably comprises a capillary or open tubular column such as a wall-coated open tubular or support-coated open tubular column, or another suitable separation element. The capillary column preferably comprises a wall-coated open tubular column having an internal diameter of about 0.18 mm (millimeters) to about 0.25 mm. The capillary column is preferably coated with a material comprising fused silica or another suitable material. The capillary column is preferably coiled and about twenty (20) meters in length. The combined gas chromatography and mass spectrometer apparatus 70 further comprises a mass spectrometer 78 coupled to the separation element 76 via connector element 77. The mass spectrometer 78 combines a high sensitivity with being able to determine the molecular composition of the portion 60 of the polar solvent 24. The combined gas chromatography and mass spectrometer apparatus 70 further comprises a gas chromatography portion 74. Preferably, the gas chromatography portion 74 comprises an oven that can be heated to a temperature of from about 130 degrees C. (Celsius) to about 250 degrees C. depending on the material being heated. The combined gas chromatography and mass spectrometer apparatus 70 analyzes the portion 60 of the polar solvent 24 to monitor for the presence of any phosphate esters 40 and to obtain an actual concentration level 82 of any phosphate esters 40 present in the jet fuel test sample 42. The in-line system 20 further comprises a calibration concentration standard 100 of phosphate esters 40 in clean jet fuel 102 for comparing to the actual concentration level 82 of any phosphate esters 40 present in the jet fuel test sample 42. The in-line system 20 further comprises a controller 80 for controlling the combined gas chromatography and mass spectrometer apparatus 70. The controller 80 preferably comprises a computer or another suitable controller device. The in-line system 20 monitors for the presence of phosphate esters in jet fuel at a concentration level of less than one (1) part per million (ppm).

EXAMPLES

Calibration standard concentrations were first prepared with known clean jet fuel in a laboratory setting and then analyzed with a laboratory combined gas chromatography and mass spectrometer apparatus to determine actual concentration levels of phosphate esters.

Materials Required. The materials required in preparing the calibration standards included clean jet fuel, petroleum ether (PET), acetonitrile (ACN), 50 ml (milliliter) PET square bottles, 100 ml glass bottles for standard preparation, balance accurate to 4 decimal places, disposable glass transfer pipettes, two 25 ml graduated cylinders, volumetric pipettes in 3 ml, 15 ml and 25 ml volumes, 2 ml gas chromatography (GC) vials. All calibration standards were prepared using known clean jet fuel and were made weight to weight in 100 ml glass bottles. Exact concentration values were made after weighing.

Extraction Procedure for Calibration Standards and Samples. 25 ml of clean jet fuel was poured in a 50 ml PET square bottle. 15 ml of PET were added by 15 ml volumetric pipette to the 50 ml PET square bottle with the 25 ml of clean jet fuel. 3 ml of ACN were added by 3 ml volumetric pipette to the 50 ml PET square bottle with the 25 ml of clean jet fuel. The 50 ml PET square bottle was capped tightly and shaken or agitated for one (1) second. Pressure was released from the 50 ml PET square bottle and the 50 ml PET square bottle was capped tightly and shaken or agitated again for one (1) second. The 50 ml PET square bottle with the 25 ml of clean jet fuel, the 15 ml of PET, and the 3 ml of ACN was placed in a shaker table and the shaker table was turned on to a fast speed, and the 50 ml PET square bottle was shaken or agitated for ten (10) minutes. The 50 ml PET square bottle was then positioned so that the ACN collected in a corner of the 50 ml PET square bottle. A 3 ml volumetric pipette was used to pipette out a portion of the ACN, and the ACN was transferred into a 2 ml gas chromatography vial. The calibration standards were then run on the combined gas chromatography and mass spectrometer apparatus and the response factors (the electronic signal produced for the phosphate ester) and standard concentrations were updated. Since concentrations were based on a "weighted" amount of SKYDROL LD-4, the standard concentration, rather than being, for example, 0.5 ppm, could be 0.52 ppm.

FIG. 5 is an illustration of a table showing the results of the calibration standards and samples prepared in the laboratory preparation and analysis procedure. FIG. 5 shows in the first column the calibration standard by weight (grams) was a 500 ppm (parts per million) stock solution of SKYDROL LD-4 in clean jet fuel where 0 (zero) was clean jet fuel, 0.50 ppm was 50% lower than the detection limit (reporting limit of less than one (1) ppm). The method for determining the MDL (Method Detection Limit) was to analyze seven (7) samples of concentration near the expected limit of detection. The standard deviation was then determined. The one sided "t" distribution was determined and multiplied versus the determined standard deviation. For seven (7) samples (with six (6) degrees of freedom), the t value for a 99% confidence interval was 3.14, 1.0 ppm was 0% lower than the detection limit, 2.5 ppm was 2.5 times higher than the detection limit, and 5.0 ppm was 5 times higher than the detection limit. FIG. 5 shows in the second column the Mass LD-4 in gm (grams) where LD-4 was Type IV, Class 1, fire resistant aviation hydraulic fluid SKYDROL obtained from Solutia Inc. of St. Louis, Mo. SKYDROL LD-4 is a low density fluid with an average concentration of 58.2% by weight of tributyl phosphate, 20-30% by weight dibutyl phenyl phosphate, 5-10% by weight butyl diphenyl phosphate, less than 10% by weight 2-ethylhexyl 7-oxabicyclo[4.1.0]heptane-3-carboxylate, and 1-5% by weight 2,6-di-tert-butyl-p-cresol. SKYDROL LD-4 has a specific gravity of 1.004-1.014 at 25 degrees Celsius, a viscosity of 10.8-11.6 cSt (CentiStokes) at 38 degrees Celsius, a flash point of 160 degrees Celsius, and an autoignition temperature of 398 degrees Celsius. The mass of the stock solution in gm (of the LD-4 in jet fuel, the 500 ppm stock) was 0, 0.05, 0.10, 0.25, and 0.50 as measured on a five (5) place balance. FIG. 5 shows in the third column the Mass Jet Fuel in gm (grams) where Jet Fuel was clean jet fuel. The mass of the Jet Fuel in gm was 50, 49.95, 49.9, 49.75, and 49.5 as measured on a five (5) place balance FIG. 5 shows in the fourth column the actual concentration in ppm wt was 500 ppm. The actual concentration in ppm wt was 0, 0.5, 1.0, 2.5, and 5.0 as measured on a five (5) place balance. Exact concentration values were made after weighing.

Combined Gas Chromatography and Mass Spectrometer Analysis for Calibration Standards and Samples. The calibration standards and samples were then analyzed with the combined gas chromatography and mass spectrometer apparatus which was obtained from Agilent Technologies, Inc. of Santa Clara, Calif. The instrument control parameters for the combined gas chromatography and mass spectrometer apparatus were set as follows:

(1) Sample Inlet—GC (Gas Chromatography); (2) Injection Source—GC ALS (Gas Chromatography Automated Liquid Sampler); (3) Mass Spectrometer—Enabled; (4) Oven—Equilibration Time 0.1 minute, Oven Program On for 130° C. (Celsius) for 1 minute then 10° C./min to 215° C. for 0 min, Run Time 9.5 minutes; (5) Front Injector—Syringe Size—10 µL (micro liter), Injection Volume—1 µL, Injection Repetitions—1, Solvent A (ACN) Washes (PreInjection)—0, Solvent A Washes (Postinjection)—4; Solvent A Volume—8 µL, Solvent B (ACN) Washes (PreInjection)—0; Solvent B Washes (Postinjection)—4, Solvent B Volume—8 µL, Sample Washes—2, Sample Wash Volume—8 µL, Sample Pumps—4, Dwell Time (PreInjection)—0 min, Dwell Time (Postinjection)—0 min, Solvent Wash Draw Speed—300 µL/min, Solvent Wash Dispense Speed—6000 µL/min, Sample Wash Draw Speed—300 µL/min, Sample Wash Dispense Speed—6000 µL/min, Injection Dispense Speed—6000 µL/min, Viscosity Delay—2 seconds, Sample Depth Disabled; (6) Back Injector (not turned on but available to use), Front SS (Split/Splitless) Inlet He (Helium), Mode—Split, Heater—On 250° C., Pressure On 32.125 psi (pounds per square inch), Total Flow—On 28.624 mL/min, Septum Purge Flow—On 3 mL/min, Gas Saver—On 20 mL/min after 2 min, Split Ratio—20:1, Split Flow—24.404 mL/min, Thermal Aux 2 {MSD (Mass Spectrometer Detector) Transfer Line}, Heater—On, Temperature Program—On 280° C. for 0 min, Run Time—9.5 min; (7) Column #1 (Capillary Column)—DB-5 ms (column type—5% phenyl, 95% methylpolysiloxane): 764.42409, DB-5 ms—325° C.: 20 m (meter) by 180 µm (micrometer) by 0.18 µm, In: Front SS Inlet He, Out: Vacuum; (8) Initial Starting Oven Parameters—Temperature—130° C., Pressure—32.125 psi, Flow—1.2202 mL/min, Average Velocity—51.082 cm/sec (centimeter per second), Holdup Time—0.65255 min, Flow Program—Off—1.2202 mL/min for 0 min, Run Time—9.5 min; (9) Front Detector FID (Flame Ionization Detector) (not turned on or used with this laboratory testing and procedure), Heater—Off, $H_2$ Flow—Off, Air Flow—Off, Makeup Flow—Off, Const Col (constant column flow) plus Makeup—Off, Flame—Off, Electrometer—Off, Signals, Test Plot—Save Off, Front Signal—Save Off, Test Plot—Save Off, Test Plot—Save Off; (10) MS (Mass Spectrometer) Acquisition Parameters—Tune File—atune.u, Acquisition Mode—Scan/SIM in FastScan mode; (11) MS Information—Solvent Delay—4.50 min, EMV (Electromagnetic Voltage) Mode—Gain Factor, Gain Factor—1.00, Resulting EMV—1600; (12) Scan Parameters—Low Mass—50.0, High Mass—450.0, Threshold—150, Sample #—0, A/D (analog to digital) Samples—1; (13) Sim Parameters—GROUP 1-Group ID—TBP (tertiarybutylphosphine), Resolution—Low, Plot 1 Ion—98.80, Ions/Dwell In Group—(Mass, Dwell—98.80, 100), GROUP 2-Group ID—PDBP (phenyl di-butyl phosphate), Resolution—High, Group Start Time—7.10, Plot 1 Ion—175.10, Ions/Dwell In Group—(Mass, Dwell—175.10, 100); (14) Data Filters—Mass Filter, Time Filter—Standard; (15) MSZones—MS Source—230 degrees C. with maximum 250 degrees C., MS Quad—150 degrees C. with maximum 200 degrees C.; (16) Tune Parameters for SN: US80828912—Trace Ion Detection is ON, EMISSION—34.610, ENERGY—69.922, REPELLER—16.385, IONFOCUS—90.157, ENTRANCE LE—32.000, EMVOLTS—1623.529, Actual EMV—1600, GAIN FACTOR—0.97, AMUGAIN—1629.000, AMUOFFSET—123.313, FILAMENT—1.000, DCPOLARITY—1.000, ENTLENSOFFS—18.573, MASSGAIN—810.000, MASSOFFSET—35.000.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A method of monitoring for the presence of phosphate esters in jet fuel, the method comprising:
   obtaining from a jet fuel source a jet fuel test sample;
   combining the jet fuel test sample with a polar solvent and a nonpolar solvent to form a mixture;
   agitating the mixture;
   performing a single extraction of a portion of the polar solvent from the mixture;
   performing one injection of the extracted portion of the polar solvent into a gas chromatography and mass spectrometer apparatus;
   performing a combined gas chromatography and mass spectrometer analysis of the polar solvent to monitor for the presence of any phosphate esters at a concentration level of less than one (1) part per million (ppm) and to obtain an actual concentration level of any phosphate esters; and,
   comparing the actual concentration level of any phosphate esters with a calibration standard concentration of phosphate esters in clean jet fuel.

2. The method of claim 1, wherein the method is performed with an in-line system on an aircraft.

3. The method of claim 2, wherein the jet fuel test sample is obtained from an aircraft in real time while the aircraft is in flight.

4. The method of claim 1, wherein the method is performed with a field kit on a ground-based airport fuel supply system.

5. The method of claim 4, wherein the jet fuel test sample is obtained from an aircraft that is being supplied with jet fuel from the airport fuel supply system or obtained directly from the airport fuel supply system.

6. The method of claim 1, wherein the polar solvent is selected from the group consisting of acetonitrile (ACN).

7. The method of claim 1, wherein the nonpolar solvent is selected from the group consisting of petroleum ether (PET).

8. The method of claim 1, wherein the combined gas chromatography and mass spectrometer analysis is performed in an amount of time in a range of from about 5 minutes to about 10 minutes.

9. The method of claim 1, wherein performing the combined gas chromatography and mass spectrometer analysis is performed with a portable combined gas chromatography and mass spectrometer apparatus.

* * * * *